United States Patent
Gandy et al.

(10) Patent No.: US 6,215,026 B1
(45) Date of Patent: Apr. 10, 2001

(54) PREPARATION OF SUBSTITUTED PHOSPHIDE SALTS

(75) Inventors: Robert Gandy, Livrpool; Peter John Cremins, Manchester; Allan William Timms, South Wirral, all of (GB)

(73) Assignee: Great Lakes (UK) Limited, Gheshire (GB)

( * ) Notice: Subject to any disclaimer, the term of this patent is extended or adjusted under 35 U.S.C. 154(b) by 0 days.

(21) Appl. No.: 09/381,985

(22) PCT Filed: Mar. 25, 1998

(86) PCT No.: PCT/GB98/00909

§ 371 Date: Jan. 11, 2000

§ 102(e) Date: Jan. 11, 2000

(87) PCT Pub. No.: WO98/43986

PCT Pub. Date: Oct. 8, 1998

(30) Foreign Application Priority Data

Mar. 27, 1997 (GB) .................................................. 9706460

(51) Int. Cl.⁷ ....................................................... C07F 9/02
(52) U.S. Cl. .................................................. 568/17; 568/8
(58) Field of Search ................................... 568/13, 17, 8; 423/179

(56) References Cited

U.S. PATENT DOCUMENTS

| 5,288,912 | 2/1994 | Devon | 568/17 |
| 5,354,894 | 10/1994 | Devon | 568/17 |
| 5,776,369 | * 7/1998 | Dover et al. | 252/309 |
| 5,777,169 | * 7/1998 | Layman, Jr. et al. | 568/17 |
| 5,866,720 | * 2/1999 | Layman, Jr. et al. | 568/17 |

FOREIGN PATENT DOCUMENTS

| 0 499 328 A2 | 8/1992 | (EP) . |
| 0 286 196 A2 | 10/1998 | (EP) . |
| WO 94/18211 | 8/1994 | (WO) . |

OTHER PUBLICATIONS

J. Org Chem by Ashby et al 58 pp 5832–5837, Oct. 1993.*
Aldrich Chem Catalogue pp 1324–1325, 1996.*

* cited by examiner

*Primary Examiner*—Jean F. Vollano
(74) *Attorney, Agent, or Firm*—Marshall, O'Toole, Gerstein, Murray & Borun

(57) ABSTRACT

Substituted sodium salts of phosphides are prepared by reacting a triarylphosphine with sodium in an aliphatic amine or diamine as a solvent or co-solvent. The resultant phosphides may be further treated with appropriate halides to produce unsymmetrical phosphines.

32 Claims, No Drawings

PREPARATION OF SUBSTITUTED PHOSPHIDE SALTS

This application is the national phase of PCT/GB98/00909, now WO98/43986.

The present invention relates to a process for preparing substituted sodium salts of phosphides and use of such salts in preparing phosphines.

The preparation of alkali metal diarylphosphides and their subsequent conversion to unsymmetrical triarylphosphines is well-known in the literature. Triarylphosphines are widely used as ligands to transition metals to afford useful catalysts for many different chemical reactions. Examples of these reactions, which are carried out on an industrial scale, include the hydroformylation reaction to produce aldehydes from alkenes, the reaction of aryl halides or alkenes to produce esters and the metathesis of simple alkenes to higher olefins. Although triphenylphosphine is frequently used as such a ligand, better specificity is often encountered if unsymmetrical triarylphosphines or diarylalkyl are used.

Methods which have been used to produce alkali metal diphenylphosphides are low yielding, difficult to carry out on a large scale, and/or expensive. For example, Hewertson and Watson (J. Chem. Soc. 1962. 1490) teach that sodium diphenylphosphide may be prepared in >75% yield by the cleavage of triphenylphosphine with sodium metal at −75° C. in liquid ammonia. Whilst such reactions are common place in the laboratory, large scale production is hampered by the need of special (and very expensive) plant which can work at these low temperatures. Issleib and Frohlich (Z. Naturforsch, 1959, 14b, 349) have shown that the reaction may be carried out with sodium metal in dioxane. However, in this case the yield is only 25%. Clearly such a low yield is unacceptable for industrial production. Finally, metallic sodium may be reacted with chlorodiphenylphosphine (Hewertson, ibid). However, chlorodiphenylphosphine, although commercially available, is somewhat expensive and is only used because there is little alternative.

There is thus a need for a method of preparing alkali metal diarylphosphides which is high yielding, uses inexpensive and readily available raw materials and uses what may be termed "conventional" chemical plant.

It has now been surprisingly found that these requirements may be met if a reaction is carried out between a readily available triarylphosphine, typically triphenyl phosphine, and an alkali metal, typically sodium, in either a primary aliphatic amine or diamine either alone or diluted with a co-solvent.

According to the present invention there is provided a process for preparing sodium diaryl salts of phosphides of general formula (I)

$$R_2P^-Na^+ \qquad (I)$$

where R is a phenyl or substituted phenyl group, by reaction of a triarylphosphine with sodium in an aliphatic amine or diamine as solvent or co-solvent.

The sodium used in the process of the invention is preferably finely dispersed in a carrier liquid. The liquid carrier may be an inert organic solvent whose boiling point is above the melting point of sodium such as, for example, toluene, xylene and petroleum ethers. Alternatively, the carrier liquid may be a mineral oil such as, for example, selected from the Shell Ordina or BP Enerpar range of high grande mineral oils.

The dispersion of sodium may be prepared by melting sodium metal in the carrier liquid and stirring rapidly. The sodium in the dispersion preferably has an average particle size in the range of 0.1 to 1000 microns, especially 0.1 to 20 microns. The sodium is preferably dispersed in an amount of 1 g of sodium per 0.1 to 100 cm³, especially 0.1 to 5 cm³ of liquid carrier.

A preferred solvent is ethylenediamine. A preferred co-solvent when used is selected from hydrocarbons and ethers. The hydrocarbon co-solvent may be aromatic or aliphatic. Toluene is an example of a suitable aromatic hydrocarbon co-solvent and hexane is an example of a suitable aliphatic hydrocarbon co-solvent. Examples of suitable ether co-solvents for use in the process of the invention include tetrahydrofuran, methyl-butyl ether and glyme ethers.

The reaction may be carried out in the temperature range of about 0° C. to about 120° C., preferably in the range of 50–70° C.

The sodium diaryl of phosphides prepared according to the invention may be further treated by reaction with a compound of the general formula $R^1X$, where $R^1$ is selected from hydrogen, phenyl or substituted phenyl (aryl) groups, naphthyl or substituted naphthyl groups, heterocyclic rings, $C_{1-10}$ carbon chains optionally containing branches or unsaturated linkages, or $-(CR^1R^1)_n PRR$ where n=1 to 10 and X is a suitable leaving group, such as halide, methoxide or nitro, to produce phosphines of the general formula.

(II)

The reaction temperature for producing unsymmetrical phosphines is preferably in the range of 0–120° C., especially 20–30° C.

The by-product from this cleavage is phenyl sodium which is a very strong base. Since this strong base may interfere with subsequent reactions, it is preferable to destroy this reagent before further chemistry is carried out. This has been carried out in the literature by the addition of ammonium salts such as ammonium chloride. In our case this is not convenient since such ammonium salts are insoluble in the reaction medium. A more convenient method of destruction is by the addition of an alcohol, such as n-butanol. Although this procedure produces sodium alkoxides and benzene these by-products do not appear to interfere with subsequent reactions.

The use of ethylenediamine has a further benefit in the subsequent reaction of the sodium diarylphosphide with a suitable electrophile in that it is an excellent solvent for conducting such reactions. Thus, the reaction may be brought about by adding the relevant alkyl or activated aryl halide, either alone or in a suitable co-solvent, to the reaction mixture and heating for an appropriate time to complete the reaction. Work-up of the final product is particularly easy by the cautious addition of water to the reaction medium. The solvent, ethylenediamine, and the inorganic by-products are soluble in water and the product simply precipitates from solution. The product may be isolated in a high degree of purity by simple filtration, washing and drying.

A particular advantage of the process of the invention is that cryogenic plant is not required and the process is easily operable in standard chemical plant on a large scale. The invention is particularly useful for preparing sodium salts of diarylphosphides, especially sodium diphenylphosphides, and then further treatment to produce unsymmetrical triarylphosphines. An advantage of the invention in relation to sodium salts is that sodium diphenylphosphide is soluble in the ethylenediamine solvent and so is tractable in subsequent reactions to give the corresponding unsymmetrical phosphine.

The invention will now be further described by means of the following Examples.

EXAMPLE 1

Preparation of Sodium Diphenylphosphide

A dispersion of sodium in mineral oil (25.4 g of 33% w/w dispersion, 0.364 mol) was added portionwise over 30 mins to a stirred suspension of triphenylphosphine (44.0 g, 0.168 mol) in ethylenediamine (50 cm$^3$) under nitrogen at 30° C. On initial addition of the dispersion an immediate exotherm occurred and the reaction mixture turned orange in colour. On addition of further portions of the dispersion, the exothermic reaction caused the internal reaction mixture temperature to rise to 70° C. and the reaction mixture to turn deep red in colour. Upon completion of dispersion addition the reaction mixture was stirred for a further 1 to 2 hours at 50–70° C. to ensure completion of reaction to afford a thick, deep red mobile reaction mixture containing sodium diphenylphosphide and phenyl sodium. The reaction mixture was then treated dropwise with butanol (12.0 g) at 50° C. to destroy phenyl sodium and stirred at 40–50° C. for a further hour. The reaction mixture produced in this way may be used directly in further reactions without any further treatment.

EXAMPLE 2

Preparation of 2-(Diphenylphosphino) Pyridine

A solution of 2-chloropyridine (19.0 g, 0.167 mol) in toluene was added dropwise to the material produced in Example 1 at 15–25° C. over 30 mins. The resulting exotherm was controlled by means of an ice bath. The colour of the reaction first turned dark brown before turning beige. On completion of the reaction, the mixture was stirred for a further 30 mins to ensure completion of reaction. Water (150 cm$^3$) was then cautiously added to afford a creamy yellow reaction mixture. The mixture was cooled to 0–5° C. and then filtered, washed with water and dried. The product was obtained as a cream coloured solid which was fairly pure. Yield=31.0 g (70% based on triphenylphosphine).

EXAMPLE 3

Preparation of Sodium Diphenylphosphide

In this Example a co-solvent is used in the process.

A dispersion of sodium in mineral oil (25.4 g of 33% w/w dispersion, 0.364 mol was added portionwise over 30 mins to a stirred suspension of triphenylphosphine (44.0 g, 0.168 mol) in ethylenediamine (90 cm$^3$) and toluene (30 cm$^3$) under nitrogen at 30° C. On initial addition of the dispersion an immediate exotherm occurred and the mixture turned orange in colour. On addition of further portions of the dispersion, the exothermic reaction caused the internal reaction mixture temperature to rise to 70° C. and the reaction mixture turn deep red in colour. Upon completion of dispersion addition the reaction mixture was stirred for a further 1 to 2 hours at 50–70° C. to ensure completion of reaction, to afford a thin deep red mobile reaction mixture containing sodium diphenylphosphide and phenyl sodium. The reaction mixture was then treated with butanol (12.0 g) at 50° C. to quench phenyl sodium and stirred at 40–50° C. for a further hour. The reaction mixture produced in this way may be reacted with compounds of the general formula R$^1$X to prepare unsymmetrical phosphines in good yield without any further treatment.

EXAMPLE 4

Preparation of Sodium Diphenylphosphide

In this Example the mode of reagent addition is reversed and a co-solvent is used.

Thus ethylenediamine (90 cm$^3$) was added dropwise over 30 mins to a stirred suspension of a dispersion of sodium in mineral oil (25.4 g of 33% w/w dispersion, 0.364 mol), triphenylphosphine (44.0 g, 0.168 mol) and methyl$^1$-butyl ether (30 cm$^3$) under nitrogen at 30° C. On initial addition ethylenediamine an immediate exotherm occurred and the mixture turned orange in colour. On addition of further portions of ethylenediamine, the exothermic reaction caused the internal reaction mixture temperature to rise to 70° C. and the reaction mixture turn deep red in colour. Upon completion of ethylenediamine addition the reaction mixture was stirred for a further 1 to 2 hours at 50–70° C. to ensure completion of reaction, to afford a deep red mobile reaction mixture containing sodium diphenylphosphide and phenyl sodium. The reaction mixture was then treated with butanol (12.0 g) at 50° C. to quench phenyl sodium and stirred at 40–50° C. for a further hour. The reaction mixture produced in this way may be reacted with compounds of the general formula R$^1$X to prepare unsymmetrical phosphines in good yield without any further treatment.

What is claimed is:

1. A process for preparing alkali metal diaryl phosphides of general formula (I)

$$R_2P^-Na^+ \tag{I}$$

where R is a phenyl or substituted phenyl group, by reaction of the corresponding triarylphosphine with sodium in an aliphatic amine or diamine as solvent or co-solvent.

2. A process as claimed in claim 1, wherein the sodium is finely dispersed in a carrier liquid.

3. A process as claimed in claim 2, wherein the carrier liquid is an inert organic solvent whose boiling point is above the melting point of sodium.

4. A process as claimed in claim 2, wherein the carrier liquid is selected from toluene, xylene and petroleum ethers.

5. A process as claimed in claim 2, wherein the liquid carrier is a mineral oil.

6. A process as claimed in claim 2, wherein the dispersion of sodium is made by melting sodium metal in the carrier liquid and stirring rapidly.

7. A process as claimed claim 2, wherein the sodium has an average particle size in the range of 0.1 to 1000 microns.

8. A process as claimed in claim 7, wherein the sodium has an average particle size of 0.1 to 20 microns.

9. A process as claimed in claim 2, wherein the sodium is dispersed in an amount of from 1 g of sodium per 0.1 to 100 cm$^3$ of liquid.

10. A process as claimed in claim 9, wherein the sodium is dispersed in an amount of 1 g of sodium per 0.1 to 5 cm$^3$ of liquid carrier.

11. A process as claimed in claim 1, wherein the aliphatic diamine is ethylenediamine.

12. A process as claimed in claim 1, wherein the diamine is diluted with a co-solvent.

13. A process as claimed in claim 12, wherein the co-solvent is selected from hydrocarbons and ethers.

14. A process as claimed in claim 13, wherein the hydrocarbon co-solvent is aromatic.

15. A process as claimed in claim 14, wherein the aromatic hydrocarbon is toluene.

16. A process as claimed in claim 15, wherein the hydrocarbon co-solvent is an aliphatic hydrocarbon.

17. A process as claimed in claim 16, wherein the aliphatic co-solvent is hexane.

18. A process as claimed in claim 13 where the ether co-solvent is selected from tetrahydrofuran, methyl-butyl ether and glyme ethers.

19. A process as claimed in claim 1, wherein the reaction temperature is in the range of 0–120° C.

20. A process as claimed in claim 19, wherein the reaction temperature is in the range of 50–70° C.

21. A process as claimed in claim 1 including the step of adding an alcohol to the reaction medium after formation of the sodium diarylphosphide.

22. A process as claimed in claim 21, wherein the alcohol is n-butanol.

23. A process as claimed in claim 1, wherein the triarylphosphine is triphenylphosphine.

24. A process for preparing an unsymmetrical phosphine comprising reacting a sodium diarylphosphide prepared by the process of claim 1 with a compound of the general formula $R^1X$, where $R^1$ is selected from the group consisting of hydrogen, phenyl, substituted phenyl, naphthyl, substituted naphthyl, heterocyclic rings, and $C_{1-10}$ carbon chains and X is a suitable leaving group.

25. A process as claimed in claim 24, wherein in the formula $R^1X$, X is selected from the group consisting of halide, methoxide and nitro groups.

26. A process as claimed in claim 24, wherein the reaction temperature is in the range 0–120° C.

27. A process as claimed in claim 26, wherein the reaction temperature is in the range 20–30° C.

28. A process as claimed in claim 24, wherein the $C_{1-10}$ carbon chains contain a functionality selected from the group consisting of a branched chain, an unsaturated linkage, and combinations thereof.

29. A process for preparing alkali metal diaryl phosphides of general formula (I)

where R is a phenyl or substituted phenyl group, by reaction of the corresponding triarylphosphine with finely dispersed sodium in an aliphatic amine or diamine as solvent or co-solvent.

30. A process as claimed in claim 29, wherein the dispersion of sodium is made by melting sodium metal in the carrier liquid and stirring rapidly.

31. A process as claimed in claim 29, wherein the sodium has an average particle size in the range of 0.1 to 1000 microns.

32. A process as claimed in claim 31, wherein the sodium has an average particle size of 0.1 to 20 microns.

* * * * *